United States Patent
Hermannsson et al.

(10) Patent No.: US 9,537,246 B2
(45) Date of Patent: *Jan. 3, 2017

(54) BIOMETRIC BELT CONNECTOR

(71) Applicant: NOX MEDICAL, Reykjavik (IS)

(72) Inventors: Kormakur Hlini Hermannsson, Reykjavik (IS); Sveinbjorn Hoskuldsson, Reykjavik (IS)

(73) Assignee: NOX MEDICAL, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,774

(22) Filed: Jun. 8, 2015

(65) Prior Publication Data

US 2015/0280348 A1    Oct. 1, 2015

Related U.S. Application Data

(63) Continuation of application No. 13/806,834, filed as application No. PCT/IS2011/050010 on Jun. 24, 2011, now Pat. No. 9,059,532.

(Continued)

(51) Int. Cl.
*H01R 11/22* (2006.01)
*A61B 5/00* (2006.01)
(Continued)

(52) U.S. Cl.
CPC .............. *H01R 13/46* (2013.01); *A61B 5/00* (2013.01); *A61B 5/04286* (2013.01);
(Continued)

(58) Field of Classification Search
CPC ..... H01R 13/46; H01R 13/6683; H01R 11/22; H01R 13/717; H01R 43/00; H01R 43/18; H01R 13/5224; H01R 2201/12; A61B 5/00; A61B 5/04286; A61B 5/0806; A61B 5/1135; A61B 5/6804
(Continued)

(56) References Cited

U.S. PATENT DOCUMENTS 937,130 A   10/1909 Williams
1,001,054 A   8/1911 Lawrence
(Continued)

FOREIGN PATENT DOCUMENTS

DE   19941500 A1   3/2001
WO   02/02013 A1   1/2002
(Continued)

OTHER PUBLICATIONS

Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.
(Continued)

*Primary Examiner* — Abdullah Riyami
*Assistant Examiner* — Harshad Patel
(74) *Attorney, Agent, or Firm* — Workman Nydegger

(57) ABSTRACT

A belt connector is provided. The belt connector is configured to electrically connect a conductor of an electrode belt to a male portion of a snap connector electrode connected to a biometric device. The belt connector includes a frame, a fastener, and an engaging member. The frame includes a receiving hole having radial flexibility. The receiving hole is configured to receive and fasten the frame to a protrusion of the male portion of the snap connector electrode. The fastener is configured to fasten the frame to a first end of the electrode belt. The engaging member is adjacent to the receiving hole and engages the conductor of the electrode belt by the conductor passing through the receiving hole. When the male portion of the snap connector electrode penetrates the receiving hole, the conductor is forced into contact with a lateral surface of the male portion of the snap connector electrode.

25 Claims, 4 Drawing Sheets

Related U.S. Application Data

(60) Provisional application No. 61/358,472, filed on Jun. 25, 2010.

(51) Int. Cl.
*H01R 13/46* (2006.01)
*A61B 5/0428* (2006.01)
*A61B 5/08* (2006.01)
*A61B 5/113* (2006.01)
*H01R 43/00* (2006.01)
*H01R 13/6591* (2011.01)
*H01R 43/18* (2006.01)

(52) U.S. Cl.
CPC .......... *A61B 5/0806* (2013.01); *A61B 5/1135* (2013.01); *A61B 5/6804* (2013.01); *H01R 11/22* (2013.01); *H01R 13/6591* (2013.01); *H01R 43/00* (2013.01); *H01R 43/18* (2013.01); *A61B 2562/227* (2013.01); *Y10T 29/49208* (2015.01)

(58) Field of Classification Search
USPC 439/527, 860, 859, 869, 909, 268; 368/282; 600/384
See application file for complete search history.

(56) References Cited

U.S. PATENT DOCUMENTS

| | | |
|---|---|---|
| 1,115,459 A | 10/1914 | Abizaid |
| 1,193,050 A | 8/1916 | Drewiler |
| 3,092,759 A | 6/1963 | Sommer |
| 3,347,223 A | 10/1967 | Pacela |
| 3,500,823 A | 3/1970 | Richardson et al. |
| 4,373,534 A | 2/1983 | Watson |
| 4,430,777 A | 2/1984 | Takeda |
| 4,671,591 A | 6/1987 | Archer |
| 4,832,608 A | 5/1989 | Kroll |
| 5,326,272 A | 7/1994 | Harhen et al. |
| 5,331,968 A | 7/1994 | Williams et al. |
| 5,348,008 A | 9/1994 | Bornn et al. |
| 5,353,793 A | 10/1994 | Bornn |
| 6,148,486 A * | 11/2000 | Uehara ................. A44B 11/10 24/170 |
| 6,327,486 B1 | 12/2001 | Nissila et al. |
| 6,341,504 B1 | 1/2002 | Istook |
| 6,461,307 B1 | 10/2002 | Kristbjarnarson et al. |
| 6,807,438 B1 | 10/2004 | Brun Del Re et al. |
| 7,593,767 B1 | 9/2009 | Modarres |
| 7,819,710 B2 | 10/2010 | McIntire et al. |
| 8,025,539 B2 | 9/2011 | Hermannsson |
| 8,193,821 B2 | 6/2012 | Mueller et al. |
| 8,251,736 B2 | 8/2012 | McIntire et al. |
| 9,059,532 B2 * | 6/2015 | Hermannsson ........ H01R 13/46 439/527 |
| 2002/0032386 A1 | 3/2002 | Sackner et al. |
| 2002/0032388 A1* | 3/2002 | Kristbjarnarson ... A61B 5/1135 600/538 |
| 2003/0135127 A1 | 7/2003 | Sackner et al. |
| 2005/0054941 A1 | 3/2005 | Ting et al. |
| 2005/0119586 A1 | 6/2005 | Coyle et al. |
| 2006/0122528 A1 | 6/2006 | Gal |
| 2006/0258948 A1 | 11/2006 | Linville |
| 2006/0282001 A1 | 12/2006 | Noel et al. |
| 2007/0167089 A1* | 7/2007 | Gobron ................ H01R 13/025 439/860 |
| 2009/0259135 A1 | 10/2009 | Stasz |
| 2010/0060300 A1 | 3/2010 | Muller et al. |
| 2010/0075527 A1 | 3/2010 | McIntire et al. |
| 2010/0075549 A1 | 3/2010 | McIntire et al. |
| 2010/0297868 A1 | 11/2010 | Hermannsson |
| 2011/0248729 A2 | 10/2011 | Mueller |

FOREIGN PATENT DOCUMENTS

| | | |
|---|---|---|
| WO | 02080761 A2 | 10/2002 |
| WO | 2006/066566 | 6/2006 |
| WO | 2008102140 A1 | 8/2008 |

OTHER PUBLICATIONS

Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.

Stromberg, N.O.T., "Error analysis of a natural breathing calibration method for respiratory inductive plethysmography", Medical & Biological Engineering & Computing 2001, vol. 39, No. 3, May 1, 2001, pp. 310-314.

International Search Report from Corresponding International PCT Application No. PCT/IB2014/002760, Mar. 27, 2015.

International Search Report from PCT Application No. PCT/IS2010/000007, Oct. 1, 2010.

"Disposable and Accessories Catalog for Respiratory Diagnostics", CareFusion, Natus Medical Inc., 2009, 138 Pages.

Petition for Inter Partes Review of U.S. Pat. No. 9,059,532, Sep. 15, 2016.

\* cited by examiner

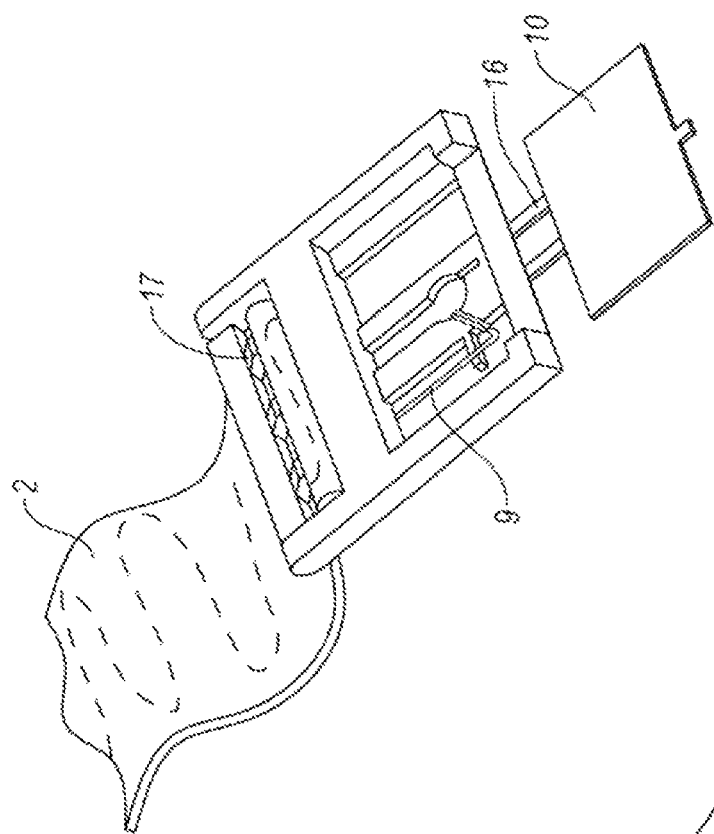
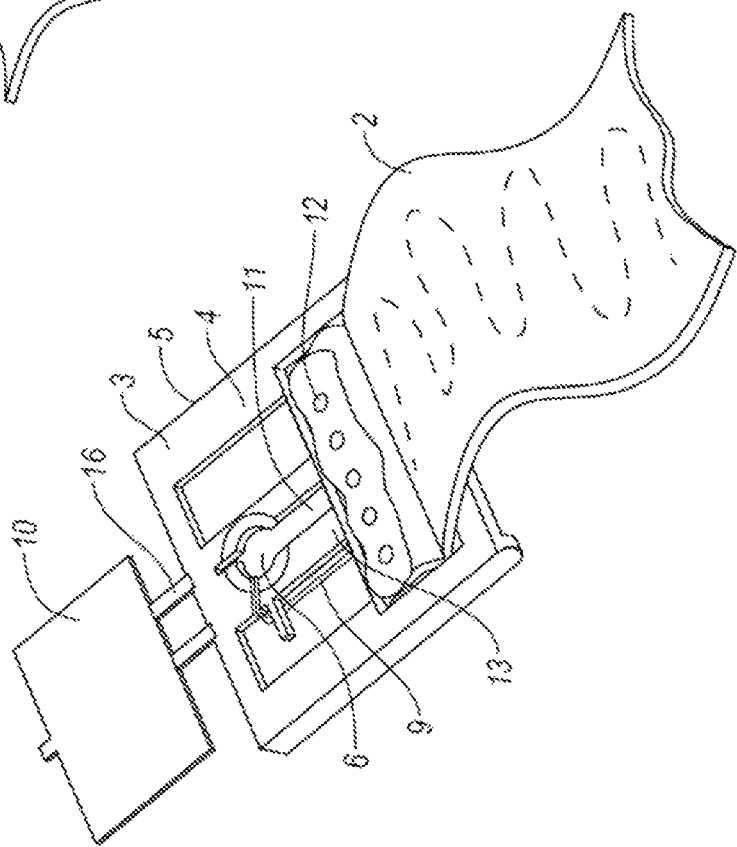
FIG. 2A
FIG. 2B

BIOMETRIC BELT CONNECTOR

This application is a continuation of U.S. patent application Ser. No. 13/806,834, filed Mar. 18, 2013, which is a 371 nationalization of Application No. PCT/IS2011/050010 filed Jun. 24, 2011, which claims the benefit of priority of U.S. Provisional Application No. 61/358,472 filed Jun. 25, 2010, the entirety of which are incorporated herein by reference.

FIELD OF THE DISCLOSURE

The present disclosure is within the field of medical devices, in particular biometric devices for measuring biosignals, and relates particularly to electrodes for such devices and in particular electrode belts and connectors for such belts.

BACKGROUND

Electrode belts are known, both for direct contact galvanic electrodes for measure cardiography signals and inductive belts used in respiratory inductive plethysmography. Prior art belts have various types of connectors, for transmitting the received signal to the respective device. There remains a need for improved belt connectors that are reliable and easy to use and maintain.

SUMMARY

The disclosure provides a belt connector for electrically connecting an electrode belt to a biometric device to be carried on a human or animal body. The belt connector is preferably made from one single piece which can be economically manufactured in order to function as a single-use consumable, to be used with a matching biometric device. The belt connector comprises a molded plastic frame having a front side and a rear side, the frame having a receiving hole, having radial flexibility to function as a female snap button fastener for receiving and fastening on the front side of the frame a male snap protrusion. The belt connector further comprises fastening means for fastening to the frame a belt end of the electrode belt, and a member adjacent to the snap fastener receiving hole to engage an electrode wire end electrically connected to the belt such that the wire end is in electrical contact with the hole, either by extending into the hole or coming in electrical contact e.g. through a bridging conductor, with a conducting male snap fastener inserted in the receiving hole.

The belt connector and belt should be configured such that a person wearing the belt under operation is insulated from current running through the belt, in order to meet existing standards for medical devices. The belt connector of the present disclosure is configured accordingly, and in a preferred embodiment, the belt connector comprises a shield member which is arranged on the rear side of the frame to electrically shield the wire end from the rear side exterior of the belt connector.

The belt connector preferably comprises a cover enclosing the connector and wire end. The cover may suitably include a pre-perforated hole overlapping the hole of the frame, or in other embodiments is made from such material that can readily be perforated by pressing the connector onto a male fastener which fits the receiving hole of the frame.

The belt end is fixedly engaged with the connector and the electrode wire connected to the connector such that the electrode wire is in electrical contact with the female snap fastener hole and thereby comes in electrical contact with a conducting male snap fastener inserted in the hole.

Preferably the belt end is engaged with the connector in a fashion allowing adjustment of the length of the belt.

BRIEF DESCRIPTION OF THE FIGURES

FIG. 1A shows a prospective top view according to the first embodiment.

FIG. 1B shows a prospective bottom view according to the first embodiment.

FIG. 1C shows a top plan view according to the first embodiment.

FIG. 1D shows a bottom plan view according to the first embodiment.

FIGS. 2A, 2B, and 2C illustrate a belt connector and connected belt according to a second embodiment.

FIG. 2A shows a prospective top view according to the second embodiment.

FIG. 2B shows a prospective bottom view according to the second embodiment.

FIG. 2C shows a prospective top view according to the second embodiment.

DETAILED DESCRIPTION

Figures 1A, 1B:
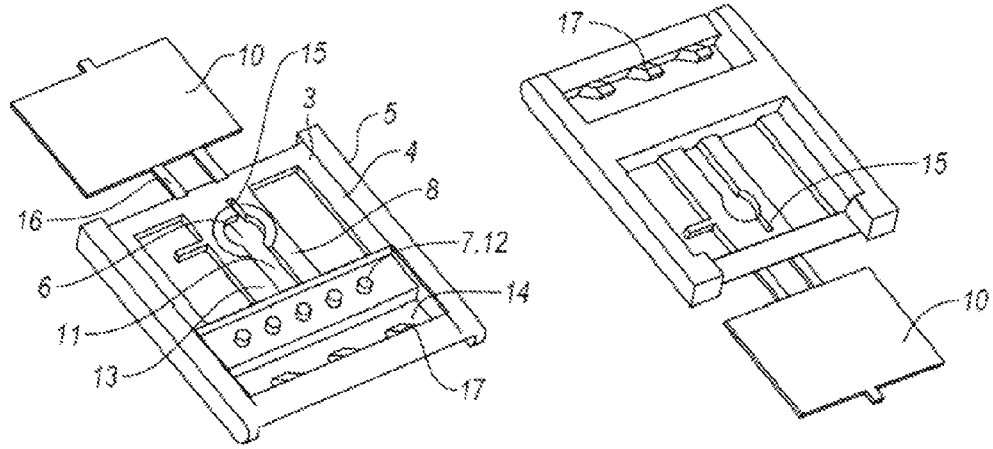
FIGS. 1A, 1B, 1C, and 1D illustrate a belt connector according to a first embodiment.

The disclosed belt connector is suitable for various types of electrode belts, such as for cardiographic measurements, both in clinical settings or for training purposes, but also for belts such as RIP (respiratory inductive plethysmography) belts.

As mentioned above, the belt connector is intended for electrically connecting an electrode belt to a biometric device, the term biometric device in this context includes any devices for receiving electrical biosignals as well as extension cables, intermediate devices, connecting boxes, etc. or other means for receiving and transmitting the biosignals.

The belt connector is preferably made from any of various suitable non-conducting plastic materials, such as but not limited to ABS (acrylonitrile butadiene styrene), PC/ABS, polyethylene, e.g. low density polyethylene (LDPE) or high density polyethylene (HDPE), or derivatives such as polyethylene terephthalate (PET) or polyfluoroethylene (PTFE), or more preferably polypropylene, polyvinyl chloride, or polyamide (nylon). In other embodiments the connector is made from paper based material or other material from natural fibers.

The electrode belt is generally a flexible belt such as commonly used in respiratory inductance plethysmography (RIP) devices today. Such electrode belt is preferably a flexible textile belt where an electrode wire is interwoven in the belt or can be laminated between two layers, typically in a zig-zag fashion to allow longitudinal elasticity.

The molded frame of the connector has a front side and a rear side, which are defined as follows: the front side of the frame faces the biometric device which is fastened onto the connector for operation and the rear side faces away from the device. In the presently preferred embodiment the rear side of the connector faces the body of the patient when mounted, i.e. the belt connector comes between the patient and the biometric device. However, the biometric device can also be configured such that the device faces the patient and the belt connectors lie on top of the device, i.e. connect to the device on the face of the device facing away from the patient, thus in such embodiment the front side of the connectors face the patient and the rear side face away from the patient.

The frame has a receiving hole with radial flexibility to function as a female snap button fastener for receiving and fastening on the front side of the frame a male snap protrusion. A mating biometric device will thus have a corresponding mating male snap fastener which can be fastened securely onto the belt connector. The hole can preferably be shaped circular or semi-circular but may in other embodiments have any other suitable shape, such as a general elongated shape shaped by two parallel members, suitably including guiding members to ensure proper positioning of the mating male snap member, a square opening, or the like.

The radial flexibility of the hole can in one embodiment be achieved by one or more slot extending from the hole. The embodiment shown if FIGS. 1 and 2 shows two slots extending across from each other in the belt direction. The one or more slot are preferably formed by at least one elongated member having flexibility transverse to its longitudinal axis (e.g. by being sufficiently thin), thus imparting flexibility to the width of the hole. Preferably the hole is between two elongated members where one or both have sufficient and suitable flexibility to provide a snap fastener hole with suitable fastening strength.

As mentioned, the belt connector comprises a member adjacent to the snap fastener receiving hole to engage an electrode wire coming from the belt end. This wire must come in electrical contact with the receiving hole, either by extending into the hole or coming in electrical contact with the hole e.g. through a bridging conductor. In one embodiment, the wire end is crimped onto the member such the crimping tubing fixes the wire and conducts and connects electrically the wire to the receiving hole, such that thus the wire and the belt is in electrical contact with a conducting male snap fastener inserted in the receiving hole.

The slot mentioned above can also function to provide an additional opening for a mating male projection on the biometric device. By this arrangement it is assured that the device cannot be incorrectly fastened, and the device will not fit any generic non-proprietary belts having connectors with female fasteners but without the correctly shaped and placed extended hole.

The connector frame has in another embodiment a separate further hole, not joined to the main fastener and electrical connection hole, where the further hole can mate with a corresponding male projection on the biometric device. Alternatively, the biometric device can have a female hole for mating with a corresponding male projection on the belt connector.

The connector frame further comprises fastening means for fastening to the frame a belt end of an electrode belt. The fastening means can in one embodiment comprise a slot with a row of teeth, pins or hooks, transverse to the belt direction, to engage a belt end. The slot preferably allows to insert through it a loop of the belt such that the belt length is adjusted and fixed, but preferably so that a user can later re-adjust the length.

In another embodiment, the fastening means comprise a ridge member, which can be a flat or sharp elongated ridge or ridge or row comprising pins or hooks, which ridge lies transverse to the belt direction and to which a belt end can be fastened onto with heat melting or gluing. Alternatively, the ridge member can have pins hooks that grab onto the belt fabric without need of heating.

Preferably, the frame has also an adjustment slot for user adjustment of the belt, which can configured with either of the two described fastening means, the adjustment slot having a row of teeth, pins or hooks transverse to the belt direction, through which adjustment slot a loop of the belt can be inserted, which hooks onto the teeth/pins when pulled on, such that the length of the belt can be readily adjusted but also secured in the desired adjusted length.

Figure 3A:
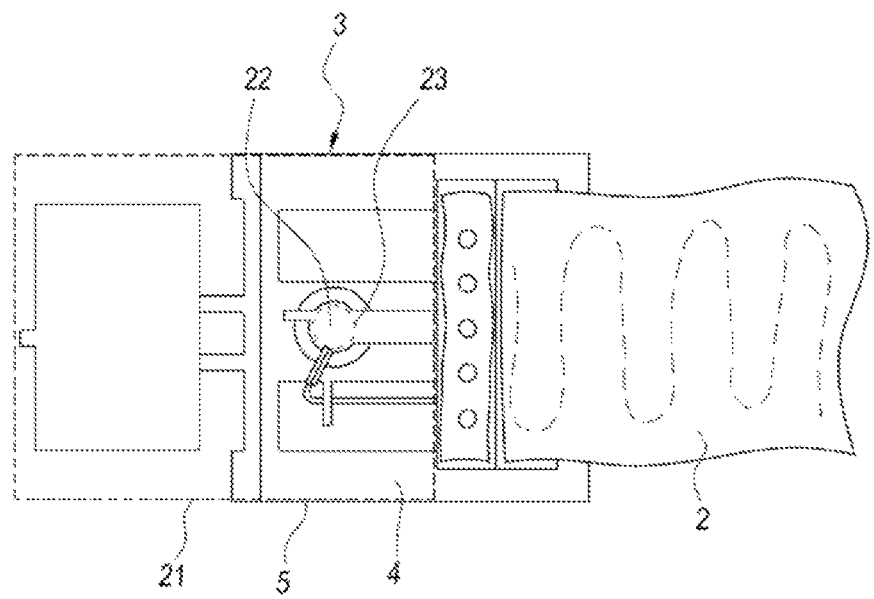
FIG. 3A shows a top plan view according to another embodiment.
Figure 3B:
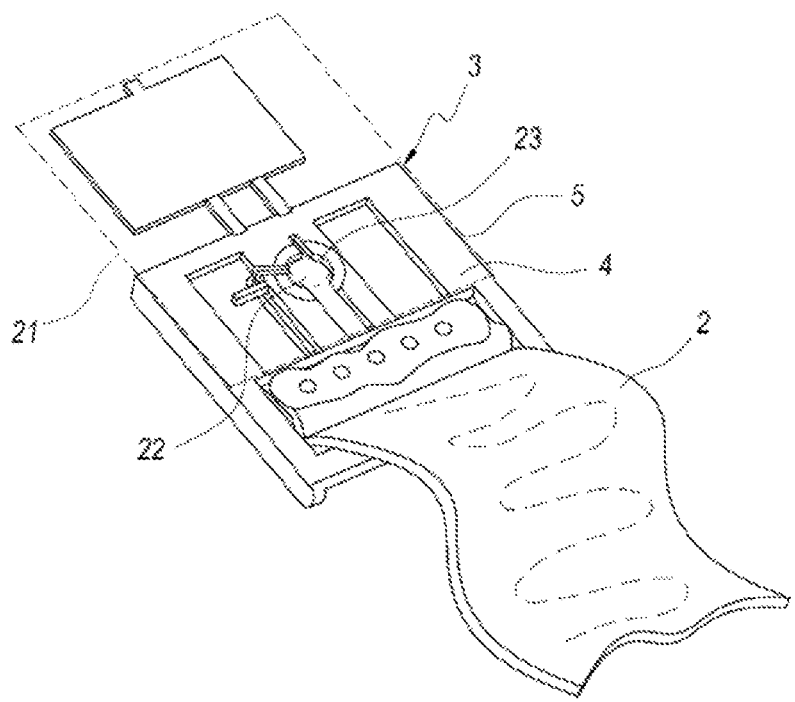
FIG. 3B shows a prospective top view according to the embodiment of FIG. 3A.

As shown in the embodiment of FIGS. 3A and 3B, the connector will preferably include a cover 21 substantially or essentially fully enclosing the frame 3, which cover 21 either includes a pre-made hole 22 overlapping the receiving hole 6 of the frame, or can be readily perforated 23 by pressing the connector onto a male fastener which fits the receiving hole 6 of the frame 3. A suitable cover can be arranged by a suitably sized paper, plastic or fabric sticker (foldable sheet with glue on one side) which sticker is folded over the frame after the belt end has been fastened and the wire end electrically connected to the receiving hole, or the cover can be from but not limited to a paper envelope, a plastic envelope and a textile envelope, which envelope is suitably fastened by gluing, sewing or the like.

In the embodiments where the biometric device has a further male projecting member which fits within the slot of the frame or within a separate mating hole, the cover is suitably arranged with corresponding openings for such hole or slot for receiving such mating male member, and the cover may also have a suitable hole allowing the protrusion of a male protruding member being a part of the frame which fits in a mating receiving hole or slot on the mating biometric device.

In a preferred embodiment, the connector comprises a shield member which is arranged on the rear side of the frame to electrically shield the wire from the rear side exterior of the belt connector. The shield member is in one embodiment a sheet member extending from the frame, which sheet member is configured to be folded over onto the rear side of the frame to cover the hole and engaged wire. Such shield member molded in one piece with the frame with enough 30 strength but suitably flexible to allow folding at least once without braking allows the use of a cover enclosing the frame, which cover need not be electrically insulating, as the shield insulates the only part of the connector which could conduct electrical current of the connector, except through the hole.

In another aspect, the present disclosure sets forth a process for making an electrode belt with biometric belt connectors, comprising:
  placing an end of a flexible electrode belt with an incorporated wire onto a belt connector as defined above, in the suitable direction in which it is to be fastened onto the connector, such that a portion of the belt end extends beyond the ridge member or row of pins,
  pressing a heat element ultrasonic hot body or other means of heat transfer onto the belt and ridge member, and through the action of the heat, shearing an end piece of the belt but leaving intact the incorporated wire, thus revealing an end of the wire,
  through the action of heat from the heat element, fastening by heat melting the belt to the ridge, and
  fastening the wire end to a member adjacent to the hole of the connector frame, such that the end is in electrical contact with the hole and comes in electrical contact with a conducting male snap fastener inserted in the hole.

The process further preferably comprises enclosing the connector frame with the fastened belt end and connected wire with a cover such as suitably a cover as described above.

FIGS. 1A, 1B, 1C, and 1D illustrate a belt connector according to a first embodiment. FIG. 1A shows a prospective top view according to the first embodiment.

Figures 1C, 1D:
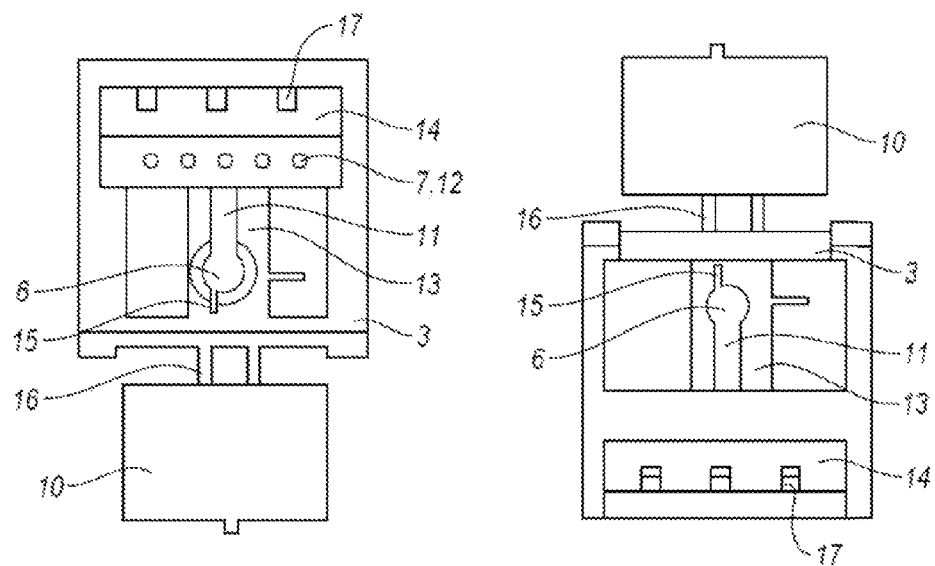

FIG. 1B shows a prospective bottom view according to the first embodiment. FIG. 1C shows a top plan view according to the first embodiment. FIG. 1D shows a bottom plan view according to the first embodiment.

Figure 2C:
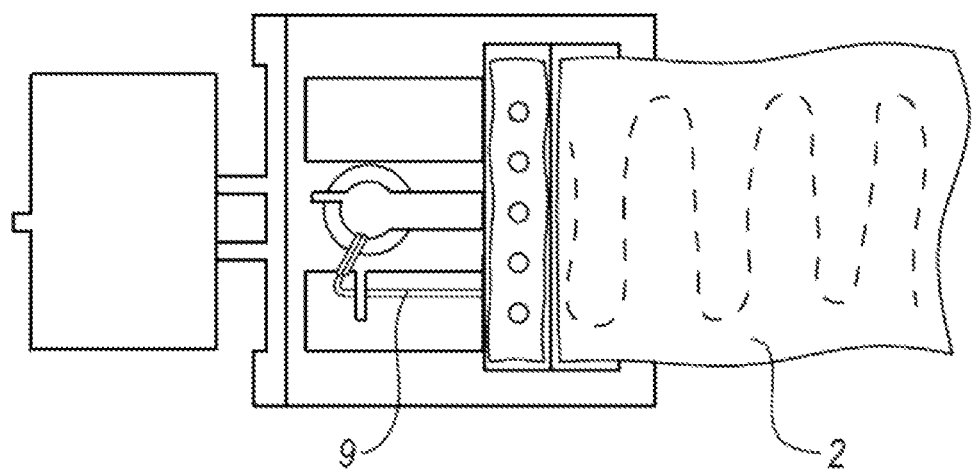

FIGS. 2A, 2B, and 2C illustrate a belt connector and connected belt according to a second embodiment.

FIG. 2A shows a prospective top view according to the second embodiment.

FIG. 2B shows a prospective bottom view according to the second embodiment.

FIG. 2C shows a prospective top view according to the second embodiment.

As seen in the first and second embodiments of FIGS. 1A, 1B, 1C, and 1D and FIGS. 2A, 2B, and 2C, respectively, a biometric belt connector (1) is electrically connected to an electrode belt (2). The connector (1) may comprise a molded plastic frame (3) having a front side (4) and a rear side (5), a shaped circular or semi-circular hole (6) with radial flexibility to function as a female snap button fastener, fastening means (7) which comprise a ridge member (12). According to the first embodiment, the ridge member (12) may include a series of buts which are provided transverse to the belt direction and to which the belt end can be fastened onto with heat melting or gluing. The frame (3) may include two members (8, 13) adjacent to the hole (6), the two members (8, 13) forming a slot (11) extending from the hole and a second slot (15) across from the first slot (11).

The elongated members and slots provide the hole with sufficient flexibility (i.e. elasticity in the width of the hole) to function as a female snap fastener. The member (13) also functions to engage an electrode wire end (9) from the belt end electrically connecting the belt with the hole and which comes in electrical contact with a conducting male snap fastener inserted in the hole. The connector further comprises a belt slot (14) with teeth members or pins (17), through which slot a loop of the belt (2) can be inserted such that it is held by the teeth/pins when pulled back, to adjust the length of the belt.

The connector further comprises a shield member (10) which may be molded in one piece with the frame (3) and joined to the frame with foldable hinges (16) such that the shield member can be folded over to cover the rear side of the hole and wire end.

What is claimed is:

1. An electrode belt and a belt connector for electrically connecting a conductor of the electrode belt to a male portion of a snap connector electrode connected to a biometric device, the belt connector comprising:
 a molded plastic frame including a receiving hole having radial flexibility, the receiving hole being configured to function as a female snap button fastener for receiving and fastening the frame to a protrusion of the male portion of the snap connector electrode,
 a fastener configured to fasten the frame to a first end of the electrode belt, and
 an engaging member adjacent to the receiving hole, the engaging member engaging the conductor of the electrode belt by the conductor passing through the receiving hole at least one, such that when the male portion of the snap connector electrode penetrates the receiving hole, the conductor is forced into physical contact with at least a lateral surface of the male portion of the snap connector electrode.

2. The electrode belt and the belt connector of claim 1, wherein the belt connector further comprises a shield member which is arranged on a rear side of the frame to electrically shield the conductor of the electrode belt from the rear side exterior of the belt connector.

3. The electrode belt and the belt connector of claim 2, wherein
 said shield member is a sheet member extending from the frame, and
 the sheet member is configured to be folded over onto the rear side of the frame to cover the back side of the receiving hole and engaged conductor.

4. The electrode belt and the belt connector of claim 1, wherein radial flexibility of the receiving hole is achieved by one or more slot extending from the hole.

5. The electrode belt and the belt connector of claim 1, wherein the receiving hole and one or more slot are formed by at least one elongated member having flexibility transverse to its longitudinal axis, thus imparting flexibility to the width of the hole.

6. The electrode belt and the belt connector of claim 1, wherein the belt connector comprises a cover enclosing the frame,
 wherein the cover defines a cover hole that overlaps the receiving hole of the frame, or the cover can be readily perforated by pressing the connector onto a male fastener which fits the receiving hole of the frame.

7. The electrode belt and the belt connector of claim 6, wherein the cover is selected from the group consisting of a folded paper, plastic or fabric sticker, a plastic envelope and a textile envelope.

8. The electrode belt and the belt connector of claim 1, wherein the fastener comprises a slot with a row of teeth, pins or hooks transverse to the belt direction, to engage a belt end.

9. The electrode belt and the belt connector of claim 1, wherein the fastener comprises a ridge member or row of pins which lies transverse to the belt direction and to which a belt end can be fastened onto with heat melting or gluing.

10. A process for making an electrode belt with a biometric belt connectors, the method comprising:
 placing an end of a flexible electrode belt with an incorporated wire onto a belt connector frame as defined in claim 9, in the suitable direction in which it is to be fastened onto the connector, such that a portion of the belt end extends beyond the ridge member or row of pins,
 pressing a heat element, ultrasonic hot body onto the belt and ridge member or row of pins, and through the action of the heat, shearing an end piece of the belt but leaving intact the incorporated wire within the end piece, thus revealing an end of the wire,
 through the action of heat from the heat element or another heat element, fastening by heat melting the belt to the ridge, and
 fastening the wire end to a member adjacent to the hole of the connector frame, such that the end is in electrical contact with the hole and comes in electrical contact with a conducting male snap fastener inserted in the hole.

11. The process of claim 10, wherein two heating steps are applied, a first heating step to shear an end piece of the belt and a second heating step to fastening the belt to the connector frame.

12. The process of claim 10, further comprising enclosing the frame with a cover and fastening the cover.

13. The electrode belt and the belt connector of claim 1, wherein the belt connector comprises an adjustment slot with teeth, pin or hook members, wherein a loop of desired length of the belt can be inserted through the adjustment slot, to adjust and fix the length of the belt.

14. The electrode belt and the belt connector of claim 1, wherein the belt is a flexible textile belt with an electrode wire interwoven in the belt or laminated between two layers of the belt.

15. The electrode belt and the belt connector of claim 1, wherein the conductor of the electrode belt is an electrode wire.

16. The electrode belt and the belt connector of claim 1, wherein the engaging member engages the conductor of the electrode belt by the conductor passing through the receiving hole by being wrapped around the engaging member.

17. The electrode belt and the belt connector of claim 1, wherein
 wherein the molded plastic frame has a front side and a back side,
 the engaging member has a first surface at the front side of the molded plastic frame and a second surface at the back side of the molded plastic frame, the first surface being on an opposite side of the engaging member from the second surface, and
 the engaging member is configured to engage the conductor of the electrode belt by the conductor passing through the receiving hole such that the conducting passes through both a plane of the first surface of the engaging member and a plane of the second surface of the engaging member.

18. The electrode belt and the belt connector of claim 1, wherein the engaging member engages the conductor of the electrode belt by the conductor passing through the receiving hole in a first pass and further the conductor of the electrode belt passing through the receiving hole in a second pass.

19. The electrode belt and the belt connector of claim 1, wherein
 an engaging member adjacent to the receiving hole, the engaging member engaging the conductor of the electrode belt by the conductor passing through the receiving hole while being wrapped around the engaging member, such that when the male portion of the snap connector electrode penetrates the receiving hole, the conductor is forced into physical contact with at least a lateral surface of the male portion of the snap connector electrode.

20. The electrode belt and the belt connector of claim 1, wherein the molded plastic frame further includes one or more slots extending from the hole, and
 the engaging member engaging the conductor of the electrode belt by the conductor passing through the receiving hole such that when the male portion of the snap connector electrode penetrates the receiving hole, the conductor is forced into physical contact with at least a lateral surface of the male portion of the snap connector electrode within the receiving hole.

21. An electrode belt with attached biometric belt connector for electrically connecting the electrode belt to a biometric device to be carried on a body of a subject, the belt connector comprising:
 a molded plastic frame having a front side and a rear side, the frame having a receiving hole with radial flexibility to function as a female snap button fastener for receiving and fastening on the frame a male snap protrusion;
 a fastener configured to fasten a belt end of the electrode belt to the frame; and
 a member adjacent to the hole, the member being configured to engage an electrode wire end electrically connected to the belt such that the wire end passes through the hole at least once and is forced into electrical contact with a lateral surface of a conducting male snap fastener when the male snap fastener is inserted into the hole.

22. The electrode belt and belt connector of claim 21, wherein the belt connector further comprises a shield member arranged on the rear side of the frame, the shield member being configured to electrically shield the wire from the rear side exterior of the belt connector.

23. The electrode belt and belt connector of claim 21, wherein radial flexibility of the receiving hole is achieved by one or more slots extending from the hole.

24. The electrode belt and belt connector of claim 23, wherein the receiving hole and one or more slot are formed by at least one elongated member having flexibility transverse to its longitudinal axis, thus imparting flexibility to the width of the hole.

25. A belt connector for electrically connecting a conductor of an electrode belt to a male portion of a snap connector electrode connected to a biometric device, the belt connector comprising:
 a frame including a receiving hole having radial flexibility, the receiving hole being configured to receive and fasten the frame to a protrusion of the male portion of the snap connector electrode,
 a fastener configured to fasten the frame to a first end of the electrode belt, and
 an engaging member adjacent to the receiving hole, the engaging member engaging the conductor of the electrode belt by the conductor passing through the receiving hole at least one, such that when the male portion of the snap connector electrode penetrates the receiving hole, the conductor is forced into physical contact with at least a lateral surface of the male portion of the snap connector electrode.

* * * * *